US011602591B2

(12) United States Patent
Cowan

(10) Patent No.: US 11,602,591 B2
(45) Date of Patent: Mar. 14, 2023

(54) CARTRIDGE-BASED IN-BORE INFUSER

(71) Applicant: BAYER HEALTHCARE LLC, Whippany, NJ (US)

(72) Inventor: Kevin P. Cowan, Allison Park, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 412 days.

(21) Appl. No.: 16/746,377

(22) Filed: Jan. 17, 2020

(65) Prior Publication Data

US 2020/0147296 A1 May 14, 2020

Related U.S. Application Data

(62) Division of application No. 14/904,888, filed as application No. PCT/US2014/046618 on Jul. 15, 2014, now Pat. No. 10,537,675.

(Continued)

(51) Int. Cl.
*A61M 5/00* (2006.01)
*A61M 5/20* (2006.01)
(Continued)

(52) U.S. Cl.
CPC ............ *A61M 5/007* (2013.01); *A61J 1/2096* (2013.01); *A61M 5/14526* (2013.01);
(Continued)

(58) Field of Classification Search
CPC .................. A61J 1/2096; A61M 5/007; A61M 5/14526; A61M 5/14546; A61M 5/20;
(Continued)

(56) References Cited

U.S. PATENT DOCUMENTS 1,367,008 A 2/1921 Bessese
3,570,486 A * 3/1971 Engelsher ........... B01F 35/7137
604/88

(Continued)

FOREIGN PATENT DOCUMENTS

EP 0945150 A2 9/1999
JP H0377070 A 4/1991
(Continued)

OTHER PUBLICATIONS

International Preliminary Report on Patentability dated Sep. 24, 2015 from corresponding PCT Application No. PCT/US2014/023214.

(Continued)

*Primary Examiner* — Quynh-Nhu H. Vu
(74) *Attorney, Agent, or Firm* — James R. Stevenson; Ryan Miller

(57) ABSTRACT

A fluid delivery device includes: a fluid-filled cartridge comprising an outlet; a syringe comprising a substantially cylindrical syringe barrel having an open end and a fluid dispensing end; and a plunger rod configured to be received within the open end of the syringe barrel. The plunger rod comprises: a first end having a sealing member provided in sealing engagement with an inner wall of the syringe barrel such that a first syringe chamber is provided between the first end of the plunger rod and the fluid dispensing end of the syringe barrel; a second end extending out of the open end of the syringe barrel and having a cartridge-receiving chamber having a connection mechanism positioned therein for connecting the outlet of the cartridge thereto. The plunger rod also includes a fluid channel extending from the connection mechanism to the first end of the plunger rod.

11 Claims, 8 Drawing Sheets

Related U.S. Application Data

(60) Provisional application No. 61/847,323, filed on Jul. 17, 2013.

(51) Int. Cl.
| | | |
|---|---|---|
| *A61M 5/145* | (2006.01) | |
| *A61J 1/20* | (2006.01) | |
| *A61M 5/315* | (2006.01) | |
| *A61B 5/055* | (2006.01) | |

(52) U.S. Cl.
CPC .......... *A61M 5/14546* (2013.01); *A61M 5/20* (2013.01); *A61M 5/204* (2013.01); *A61M 5/2053* (2013.01); *A61B 5/055* (2013.01); *A61M 5/31511* (2013.01)

(58) Field of Classification Search
CPC ................ A61M 5/204; A61M 5/2053; A61M 5/31511; A61M 5/1452; A61M 5/2066
See application file for complete search history.

(56) References Cited

U.S. PATENT DOCUMENTS

| | | | | |
|---|---|---|---|---|
| 3,724,460 | A * | 4/1973 | Gomez | A61M 5/2425 |
| | | | | 604/88 |
| 4,006,736 | A | 2/1977 | Kranys et al. | |
| 4,014,330 | A | 3/1977 | Genese | |
| 4,161,178 | A | 7/1979 | Genese et al. | |
| 4,171,698 | A * | 10/1979 | Genese | A61M 5/284 |
| | | | | 604/88 |
| 4,323,066 | A | 4/1982 | Bourdon | |
| 4,367,737 | A | 1/1983 | Kozam et al. | |
| 4,677,980 | A | 7/1987 | Reilly et al. | |
| 4,693,706 | A * | 9/1987 | Ennis, III | A45D 44/002 |
| | | | | 604/87 |
| 4,936,315 | A | 6/1990 | Lineback | |
| 5,033,650 | A | 7/1991 | Colin et al. | |
| 5,067,948 | A * | 11/1991 | Haber | A61M 5/1782 |
| | | | | 604/220 |
| 5,135,500 | A | 8/1992 | Zdeb | |
| 5,176,642 | A | 1/1993 | Clement | |
| 5,279,608 | A | 1/1994 | Cherif Cheikh | |
| 5,312,389 | A | 5/1994 | Theeuwes et al. | |
| 5,330,426 | A * | 7/1994 | Kriesel | A61M 5/2429 |
| | | | | 604/82 |
| 5,383,858 | A | 1/1995 | Reilly et al. | |
| 5,494,036 | A | 2/1996 | Uber, III et al. | |
| 5,553,619 | A | 9/1996 | Prince | |
| 5,588,556 | A | 12/1996 | Sancoff et al. | |
| 5,746,208 | A | 5/1998 | Prince | |
| 5,746,724 | A * | 5/1998 | Powles | A61B 10/0283 |
| | | | | 600/565 |
| 5,769,824 | A | 6/1998 | Hjertman et al. | |
| 5,827,262 | A | 10/1998 | Neftel et al. | |
| 5,911,252 | A | 6/1999 | Cassel | |
| RE37,602 | E | 3/2002 | Uber, III et al. | |
| 6,387,228 | B1 | 5/2002 | Maget | |
| 6,413,238 | B1 | 7/2002 | Maget | |
| 6,425,885 | B1 | 7/2002 | Fischer et al. | |
| 6,638,244 | B1 | 10/2003 | Reynolds | |
| 6,656,157 | B1 | 12/2003 | Duchon et al. | |
| 6,704,592 | B1 | 3/2004 | Reynolds et al. | |
| 6,875,203 | B1 | 4/2005 | Fowles et al. | |
| 6,923,800 | B2 | 8/2005 | Chen et al. | |
| 7,115,117 | B2 | 10/2006 | Shiraishi et al. | |
| 7,221,159 | B2 | 5/2007 | Griffiths et al. | |
| 7,283,860 | B2 | 10/2007 | Frazier et al. | |
| 7,315,109 | B1 | 1/2008 | Griffiths et al. | |
| 7,407,490 | B2 | 8/2008 | Bendsen et al. | |
| 7,632,245 | B1 | 12/2009 | Cowan et al. | |
| 7,736,353 | B2 | 6/2010 | Reynolds | |
| 9,044,545 | B2 * | 6/2015 | Hagg | A61B 17/3203 |
| 9,101,713 | B2 * | 8/2015 | Cowan | A61M 5/31515 |
| 10,543,312 | B2 | 1/2020 | Cowan | |
| 2001/0056233 | A1 | 12/2001 | Uber et al. | |
| 2002/0017484 | A1 | 2/2002 | Dourdeville | |
| 2002/0107481 | A1 | 8/2002 | Reilly et al. | |
| 2002/0115933 | A1 | 8/2002 | Duchon et al. | |
| 2002/0165490 | A1 | 11/2002 | Minezaki et al. | |
| 2003/0176833 | A1 | 9/2003 | Libermann | |
| 2003/0199787 | A1 | 10/2003 | Schwindt | |
| 2003/0236442 | A1 | 12/2003 | Connors et al. | |
| 2004/0030233 | A1 | 2/2004 | Frazier et al. | |
| 2004/0171983 | A1 | 9/2004 | Sparks et al. | |
| 2004/0181147 | A1 | 9/2004 | Prince | |
| 2004/0193045 | A1 | 9/2004 | Scarborough et al. | |
| 2005/0070848 | A1 | 3/2005 | Kim et al. | |
| 2005/0084395 | A1 | 4/2005 | Kang | |
| 2005/0107738 | A1 | 5/2005 | Slater et al. | |
| 2005/0197531 | A1 | 9/2005 | Cabiri et al. | |
| 2005/0209790 | A1 | 9/2005 | Niethammer | |
| 2006/0079834 | A1 | 4/2006 | Tennican et al. | |
| 2007/0043319 | A1 | 2/2007 | Kimmel et al. | |
| 2008/0021389 | A1 * | 1/2008 | Runfola | A61M 5/3234 |
| | | | | 604/110 |
| 2008/0097389 | A1 | 4/2008 | Wilson | |
| 2008/0167621 | A1 | 7/2008 | Wagner et al. | |
| 2010/0305507 | A1 | 12/2010 | Duncan | |
| 2011/0098657 | A1 | 4/2011 | Jennings et al. | |
| 2011/0282197 | A1 | 11/2011 | Martz | |
| 2012/0323173 | A1 | 12/2012 | Thorne, Jr. et al. | |
| 2013/0172818 | A1 | 7/2013 | Schraga | |
| 2014/0000730 | A1 | 1/2014 | Nguyen et al. | |
| 2014/0276411 | A1 * | 9/2014 | Cowan | A61B 6/481 |
| | | | | 604/143 |
| 2015/0343149 | A1 | 12/2015 | Cowan et al. | |
| 2016/0030674 | A1 * | 2/2016 | Cowan | A61M 5/48 |
| | | | | 604/227 |

FOREIGN PATENT DOCUMENTS

| | | |
|---|---|---|
| JP | A04221567 | 8/1992 |
| JP | H0520751 U | 3/1993 |
| JP | H05345024 A | 12/1993 |
| JP | U06070738 | 10/1994 |
| JP | H08511460 A | 12/1996 |
| JP | H11276581 A | 10/1999 |
| JP | 2002035125 A | 2/2002 |
| JP | 2008149119 A | 7/2008 |
| JP | 2011528574 A | 11/2011 |
| WO | 9004987 A1 | 5/1990 |
| WO | 9106338 A1 | 5/1991 |
| WO | 9201484 A1 | 2/1992 |
| WO | 9528977 A1 | 11/1995 |
| WO | 0100261 A1 | 1/2001 |
| WO | 0192907 A2 | 12/2001 |
| WO | 2006045215 A1 | 5/2006 |
| WO | 2010138170 A2 | 12/2010 |

OTHER PUBLICATIONS

International Search Report and Written Opinion dated Jun. 10, 2014 from corresponding PCT Application No. PCT/US2014/020260.

International Search Report and Written Opinion dated Jul. 8, 2014 of corresponding PCT Application No. PCT/US2014/023214.

Written Opinion and International Search Report dated Feb. 10, 2015 from related PCT Application No. PCT/US2014/046618.

"A Primer on Medical Device Interactions with magnetic Resonance Imaging Systems," accessed at http://www.fda.gov/cdrh/ode/primerf6.html, accessed on Sep. 5, 2007, pp. 15.

"A Primer on Medical Device Interactions With Magnetic Resonance Imaging Systems," U. S. Food and Drug Administration, Center for Devices and Radiological Health (Feb. 7, 1997).

"Extended European Search Report from EP Application No. 14825990", dated Mar. 2, 2017.

International Preliminary Report on Patentability and Written Opinion dated Sep. 24, 2015 from PCT Application No. PCT/US2014/020260; 7 pages.

International Preliminary Report on Patentability dated Jan. 28, 2016 from PCT/US2014/046618.

(56) References Cited

OTHER PUBLICATIONS

Keeler, E.K., et al., "Accessory Equipment Considerations with Respect to MRI Compatibility," JMRI, vol. 8, No. 1, pp. 12-18 (1998).
Lemieux, L, et al. "Recording of EEG during fMRI experiments: patient safety," Magnetic Resonance in Medicine, vol. 38, No. 6, pp. 943-952, John Wiley & Sons, Inc. (1997).
"Supplementary European Search Report from EP Application No. EP14774466", dated Oct. 5, 2016.
"Supplementary European Search Report from EP Application No. EP14779557", dated Oct. 25, 2016.
"Supplementary European Search Report from EP Application No. EP14825990", dated Feb. 20, 2017.
U.S. Appl. No. 10/916,946, filed Aug. 12, 2004, Griffiths et al.

\* cited by examiner

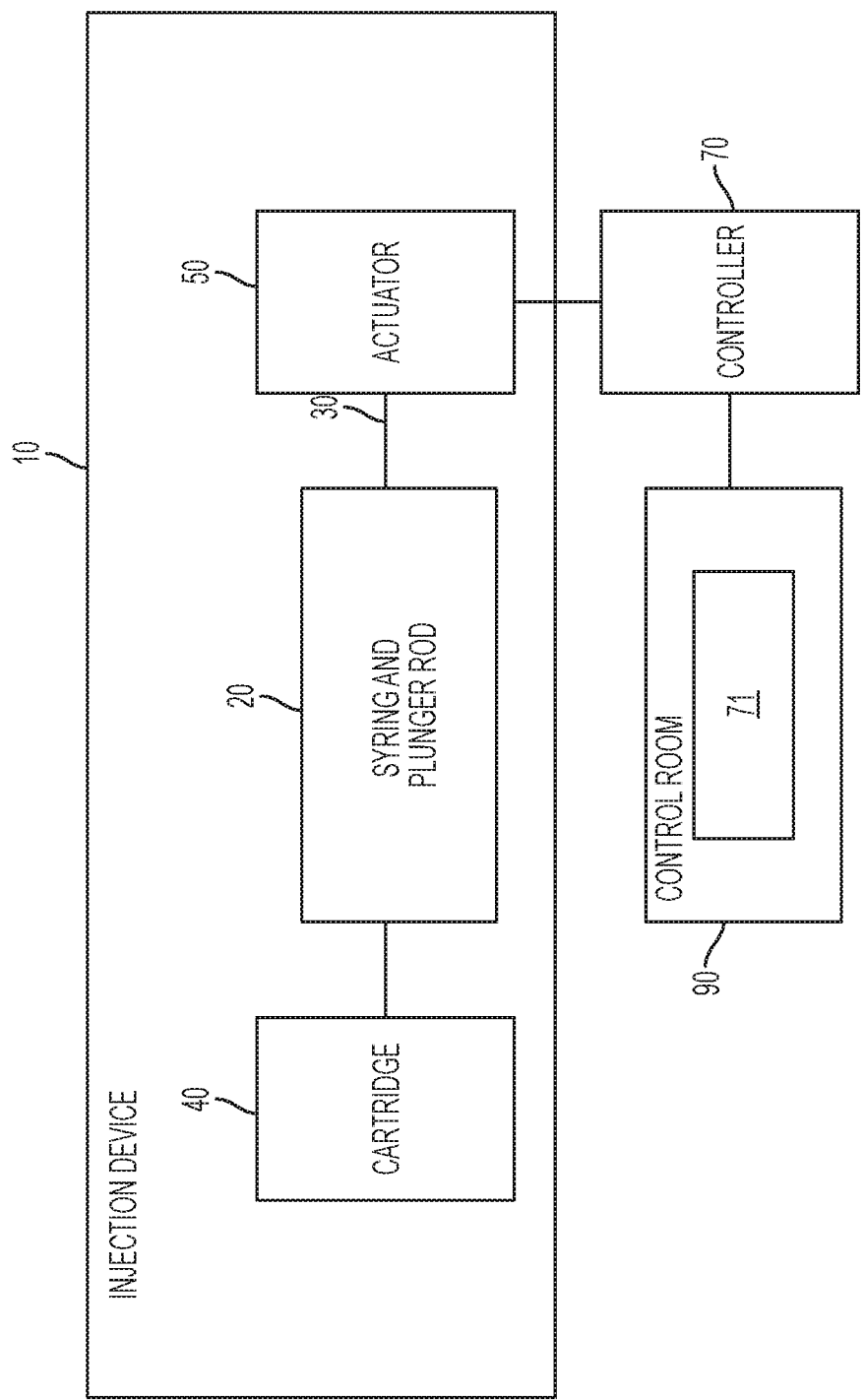

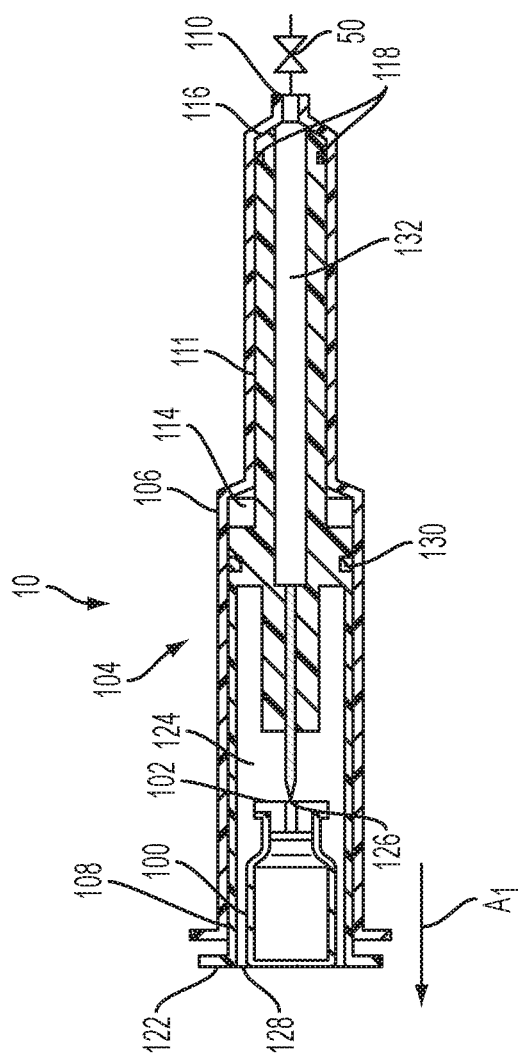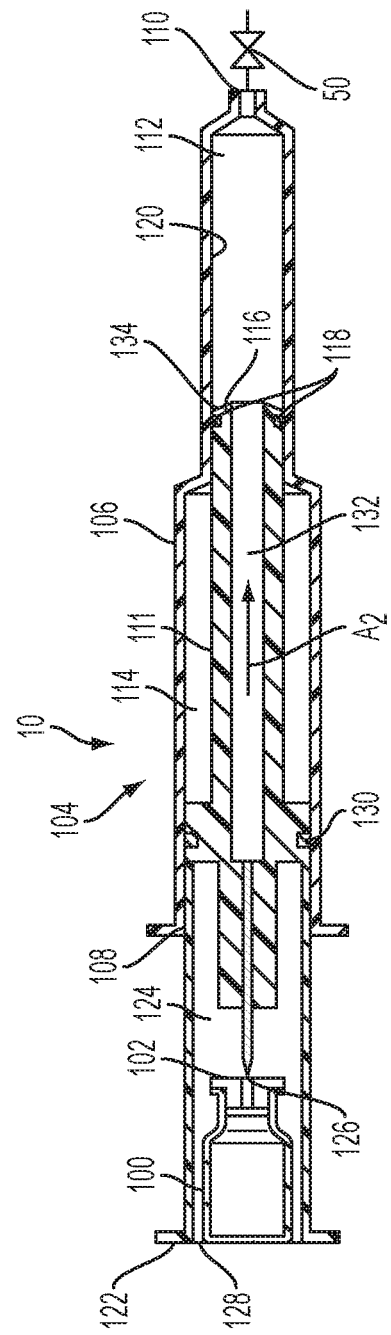

CARTRIDGE-BASED IN-BORE INFUSER

CROSS REFERENCE TO RELATED APPLICATION

This Application is a Divisional of U.S. application Ser. No. 14/904,888, filed on Jan. 16, 2016, which is a 371 national phase application of PCT International Application No. PCT/US2014/046618, filed Jul. 15, 2014, and designating the United States of America, which claims the benefit from the earlier filed U.S. Provisional Application No. 61/847,323, filed Jul. 17, 2013, entitled "Cartridge-Based In-Bore infuser," and is hereby incorporated into this application by reference as if fully set forth herein.

BACKGROUND OF THE INVENTION

Field of the Invention

The present invention relates generally to devices, systems, and methods for delivery of a fluid, and, particularly, for infusion or injection of a fluid contained in a cartridge, such as a syringe, vial, or other suitable fluid delivery device, into a patient.

Description of Related Art

A number of injector-actuated syringes and powered injectors for use in medical procedures such as angiography, computed tomography (CT), ultrasound, and NMR/MRI have been developed. U.S. Pat. No. 4,006,736, for example, discloses an injector and syringe for injecting fluid into the vascular system of a human being or an animal. Typically, such injectors comprise drive members, such as pistons, that connect to a syringe plunger. For example, U.S. Pat. No. 4,677,980, the disclosure of which is incorporated herein by reference, discloses an angiographic injector and syringe wherein the drive member of the injector can be connected to, or disconnected from, the syringe plunger at any point along the travel path of the plunger via a releasable mechanism. A front-loading syringe and injector system is also disclosed in U.S. Pat. No. 5,383,858, the disclosure of which is incorporated herein by reference.

Although significant advances have been made in the design and operation of powered injectors, a number of problems persist which can limit their use. For example, each year in the United States several million MRI procedures are performed. However, powered injectors are used in only a relatively small percentage of such procedures. In MRI procedures in which there is no need to accurately control the timing of contrast injection or the flow rate of injection, powered injectors are almost never used. In that regard, MRI procedures are relatively expensive and patient throughput is a primary concern. It is perceived that use of powered injectors in such procedures will require additional time, while providing little benefit. Thus, in contrast-enhanced procedure in which timing and flow rate control are not important, contrast is currently injected manually. Typically, the patient is placed in the MRI bore and a baseline scan is performed. The patient is then removed from the bore of the imaging device and the contrast is injected. The patient is then once again placed in the bore and the contrast-enhanced imaging is performed.

A number of problems often arise with the manual injection of contrast in an MRI procedure. For example, after injection it is often difficult to reposition the patient in the same position in which the baseline measurement was made. Even if repositioning can be achieved with success, removal of the patient from the bore to manually inject contrast and subsequent repositioning require a substantial amount of time. Moreover, in some instances, particularly with claustrophobic patients, the patient refuses to reenter the bore. Furthermore, it is sometimes difficult with some patients to properly inject the contrast manually. In such cases, it may become necessary to call for the services of an IV specialist team, greatly increasing the amount of time required for the scan.

Even in imaging procedures other than MRI procedures (such as CT, angiography, and ultrasound), there may be reluctance to use powered injectors in certain procedures because of perceived or actual burdens with such use.

For the above reasons and others, it is desirable to develop improved devices, systems, and methods for the injection of fluids into patients.

SUMMARY OF THE INVENTION

An object of the invention described hereinafter is to provide an injection device that is readily fabricated to be fully in-bore compatible for MR procedures. A further object is to provide an injection device that can, for example, be applied to a patient outside the scanning room such that there is no need to remove a patient from the scanner bore to perform an injection. An additional object is to keep the time required for set up of the devices described hereinafter minimal.

According to one aspect of the invention, a fluid delivery device includes: a fluid-filled cartridge comprising an outlet; a syringe comprising a substantially cylindrical syringe barrel having an open end and a fluid dispensing end; and a plunger rod configured to be received within the open end of the syringe barrel. The plunger rod comprises: a first end having a sealing member provided in sealing engagement with an inner wall of the syringe barrel such that a first syringe chamber is provided between the first end of the plunger rod and the fluid dispensing end of the syringe barrel; a second end extending out of the open end of the syringe barrel and having a cartridge-receiving chamber having a connection mechanism positioned therein for connecting the outlet of the cartridge thereto; and an intermediate sealing member provided in sealing engagement with the inner wall of the syringe barrel. The intermediate sealing member is positioned between the first end and the second end of the plunger rod such that a second syringe chamber is provided between the intermediate sealing member and the first end of the plunger rod. The plunger rod also includes a fluid channel extending from the connection mechanism to the first end of the plunger rod; and a one-way check valve positioned at the first end of the plunger rod. The fluid delivery device also includes an actuator connected to the fluid dispensing end of the syringe barrel. Fluid is dispensed from the cartridge by connecting the outlet of the cartridge to the connection mechanism, thereby providing the cartridge in fluid communication with fluid channel, forming a vacuum within the second syringe chamber by pulling the second end of the plunger rod away from the open end of the syringe barrel, thereby drawing fluid from the cartridge through the fluid channel and into the first syringe chamber, and switching the actuator from a first state in which fluid is prevented from flowing through the fluid dispensing end of the syringe to a second state to allow the fluid to flow through the fluid dispensing end.

In one embodiment, the fluid delivery device may be provided as a prepackaged system that is autoclaved sterilized. In such an embodiment, the fluid-filled cartridge may be a vial and the connection mechanism may be a spike. The vial may be positioned within the cartridge receiving chamber and a flexible seal may be positioned over the second end of the plunger rod. In use, the vial is engaged with a spike by pressing the flexible seal.

In an alternative embodiment, the fluid-filled cartridge may be a syringe and the connection mechanism may be a female luer connector.

The first syringe chamber may have a first diameter and the second syringe chamber may have a second diameter that is greater than the first diameter. In addition, a mechanism of the actuator may include a rotary valve, a pinch valve with tubing, a ratchet valve, a fusible link, a trumpet valve, a port closing valve, a pump system, or a drive system. The fluid delivery device may further include a controller configured to remotely control the state of the actuator. The controller may be configured to control the state of the actuator via ultrasound, via a protocol of an imaging scanner, via microwave energy, via a mechanical link, via infrared light, via fiber optic cable, via pneumatic power, via hydraulic power, via voice activation, via movement of a scanner table, via time delay, via an RF gradient trigger from a scanner, via a photo cell, via optical light, via an RF signal, or via line power.

The fluid-filled cartridge, the syringe, the plunger rod, and the actuator may be configured to be MR compatible, thereby making the device suitable for use in or near a bore of an MR scanner.

According to another aspect of the invention, a fluid delivery device includes a syringe comprising: a substantially cylindrical syringe barrel having a fluid dispensing end and an open end; and a plunger configured to be received within the open end of the syringe barrel; a drive mechanism comprising a substantially cylindrical body having a movable member positioned therein to form a chamber between the movable member and a substantially closed first end of the cylindrical body; a plunger rod connected to a first side of the movable member and extending through the substantially closed first end of the body, the plunger rod configured to operatively engage the plunger; and a locking mechanism configured to secure the open end of the syringe to the substantially closed first end of the body; and an actuator connected to the fluid dispensing end of the syringe barrel. Fluid is dispensed from the syringe by connecting the syringe to the plunger rod, forcing the open end of the syringe into the locking mechanism thereby moving the movable member towards a second end of the cylindrical body which forms a vacuum within the chamber, and switching the actuator from a first state in which fluid is prevented from flowing through the fluid dispensing end of the syringe to a second state to allow the fluid to flow through the fluid dispensing end.

According to yet another aspect of the invention, a fluid delivery device comprises: a fluid-filled cartridge comprising an outlet; a fluid container having a fluid receiving end; a connection mechanism extending from the fluid receiving end of the fluid container and comprising a fluid path extending from a first end of the connection mechanism to a second end of the connection mechanism in fluid communication with the fluid receiving end of the fluid container; a compressible member extending from the outlet of the fluid-filled cartridge to the fluid receiving end of the fluid container and surrounding the connection mechanism; and a removable retention mechanism positioned between the outlet of the fluid-filled cartridge and the fluid receiving end of the fluid container over the compressible member to prevent the outlet of the fluid-filled cartridge from contacting the connection mechanism. Fluid is transferred from the fluid-filled cartridge to the fluid container by removing the removable retention mechanism and compressing the compressible member such that the outlet of the cartridge is connected to the connection mechanism, thereby providing the cartridge in fluid communication with the fluid path extending from the first end of the connection mechanism to the second end of the connection mechanism in fluid communication with the fluid receiving end of the fluid container.

These and other features and characteristics of the device of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the device of the present disclosure. As used in the specification and the claims, the singular form of "a", "an", and "the" include plural referents unless the context clearly dictates otherwise.

BRIEF DESCRIPTION OF THE DRAWINGS

FIG. 1 is a schematic diagram of a fluid delivery device of the present invention;

FIGS. 2A-2C are a series of cross-sectional views of a first embodiment of the fluid delivery device of the present invention;

DESCRIPTION OF THE INVENTION

Figure 2C:
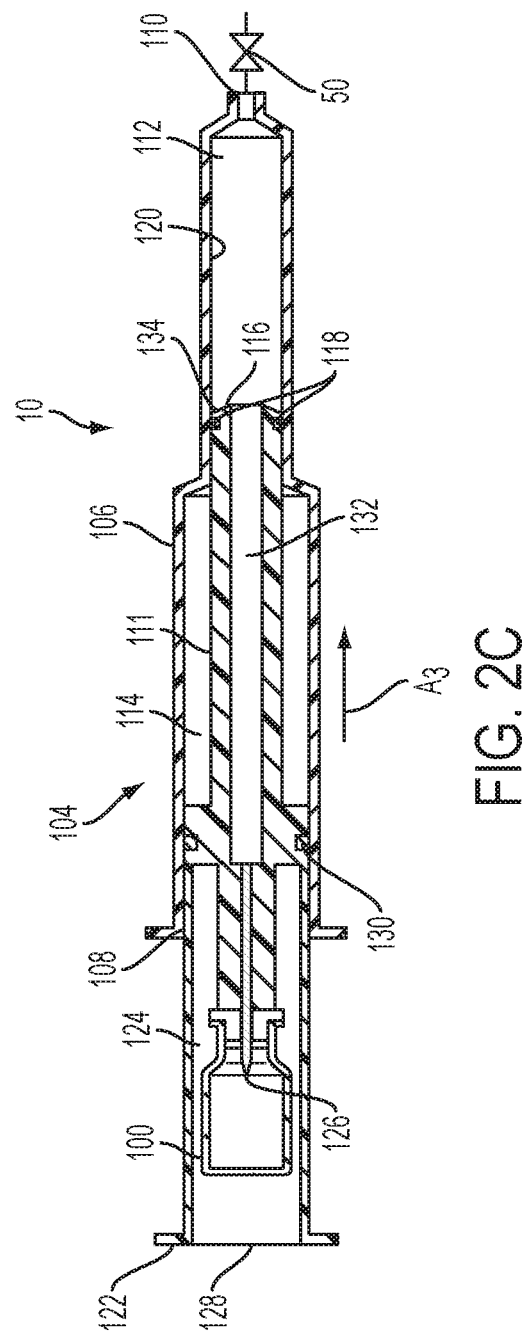

For purposes of the description hereinafter, the terms "upper", "lower", "right", "left", "vertical", "horizontal", "top", "bottom", "lateral", "longitudinal", and derivatives thereof, shall relate to the device of the present disclosure as it is oriented in the drawing figures. However, it is to be understood that the device of the present disclosure may assume various alternative variations, except where expressly specified to the contrary. It is also to be understood that the specific devices illustrated in the attached drawings, and described in the following specification, are simply exemplary embodiments of the device of the present disclosure. Hence, specific dimensions and other physical characteristics related to the embodiments disclosed herein are not to be considered as limiting.

In general, the present invention provides infusion or injection devices and systems that are relatively easy to operate. The injection devices disclosed herein are related to the injection devices disclosed in U.S. Pat. No. 7,632,245 and U.S. patent application Ser. No. 13/826,483, which are hereby incorporated by reference in their entirety.

In the embodiment of the present invention illustrated in FIG. 1, an injection or infusion device 10 includes a fluid-filled cartridge 40 (for example, a vial, a prefilled syringe, or another suitable fluid delivery device) in which a fluid for injection into a patient is stored. Injection device 10 includes an outlet 30 in fluid connection with a syringe and plunger rod combination 20 and through which fluid exits the syringe to be injected into the patient. Injection device 10 also includes the syringe and plunger rod combination 20 through which force/pressure, via a vacuum, is applied to the fluid that is drawn from the fluid-filled cartridge 40 into a portion of the syringe to cause the pressurized fluid to exit outlet 30. Injection device 10 further includes an actuator 50 to initiate (and, possibly, terminate) flow. Actuator 50 can, for example, be operated by a controller 70 via a remote controller 71 from, for example, control room 90.

The actuator 50 can, for example, include a rotary valve at a syringe tip, a pinch valve with tubing, a ratchet valve, a fusible link, a trumpet valve, a port closing valve, a pump system, or a drive system to allow fluid to flow through outlet 30. The mechanism for operating the actuator 50 (or imparting motion thereto to change a state) can, for example, include a vacuum drive, a piezoelectric drive, an electric motor drive (for example, an inside-MRI bore air core motor in which the magnet of the bore forms part of the motor), a solenoid drive, an electric motor drive outside of the bore, an electro-resistive pump, a charged ion pump (available, for example, from Exigent), a magneto restrictive material (to which a voltage is applied), a thermochemical activated motion (TCAM) material or device, a nitinol material, a state transition (liquid to gas), a bi-metallic material (with different rates of expansion for each metal), an electro-active polymeric material, pneumatic or hydraulic pressure, and/or gravity. Power can be supplied via, for example, vacuum power, chemical power, electrical power (for example, battery power, wall outlet power), power from the scanner, human/manual power, compressed or pressurized gas (for example, $CO_2$ or air) power, hydraulic power, spring power, gravity power, or light/photoelectric power. In the embodiments described hereinafter, the actuator 50 is desirably a normally-closed valve.

The controller 70 can, for example, control the state of the actuator 50 via ultrasound (for example, via a piezo tweeter operating through glass); via a scanner coil protocol (for example, GE/Siemens scanners comprise approximately 85% of the axial market and include two 15 volt connections); via microwave energy (for example, a glass smart link); via a mechanical or cable link (for example, via camera-type cable link using a plastic cable); via infrared light; via fiber optic cable; via pneumatic power; via hydraulic power; via patient operation; via voice activation; via movement of a table upon which a patient is positioned; via time delay; via an RF gradient trigger from scanner (for example, 5th shim tune); via a photo cell; via optical light control; via line power (for example, via audio frequency through panel); via an RF link, or via operator manual control (that is, sending the operator into the MRI room to activate the device).

For use in an MR environment, the components of the injection device 10 are desirably fabricated from materials that are non-magnetic, non-ferrous, and/or otherwise suitable or compatible for use in an MRI environment. In general, many devices, including but not limited to many injectors and infusion pumps, that contain electric actuators such as DC brush motors, step motors, brushless DC motors, or other wound coil motors and solenoids, often fail in a strong magnetic field as a result of damage to internal permanent magnets. Moreover, currents induced within the field windings of such devices from electromagnetic fields can cause overheating and potential damage to the windings and any connected electronic circuitry. The MRI magnetic field can also interfere with the device-created magnetic field and prevent accurate operation.

Furthermore, differences in magnetic permeability of materials within the actuator and eddy currents induced within actuator windings can affect the homogeneity or uniformity of the MRI magnetic field, generating image artifacts. Actuators that use mechanical commutation, such as DC brush motors, can also generate radio frequency energy during switching, which can induce unwanted artifacts upon the acquired MRI images.

With reference to FIGS. 2A-2C and with continued reference to FIG. 1, the injection device 10 is desirably provided as a prepackaged system that is autoclaved sterilized. The injection device 10 includes an MR contrast vial 100 (as the fluid-filled cartridge) having a septum sealed outlet 102. The injection device 10 also includes a syringe 104 having a substantially cylindrical syringe barrel 106 an open end 108 and a fluid dispensing end 110; and a plunger rod 111 configured to be received within the open end 108 of the syringe barrel 106. As discussed in greater detail hereinafter, the cylindrical syringe barrel 106 is divided into a delivery chamber 112 and a vacuum drive chamber 114. Desirably, the delivery chamber 112 may have a first diameter and the vacuum drive chamber 114 may have a second diameter that is greater than the first diameter as shown in FIGS. 2A-2C; however, this is not to be construed as limiting the present invention as both chambers may have the same diameter.

The plunger rod 111 includes: a first end 116 having a sealing member, such as O-ring 118, provided in sealing engagement with an inner wall 120 of the syringe barrel 106 to form the delivery chamber 112 between the first end 116 of the plunger rod 111 and the fluid dispensing end 110 of the syringe barrel 106; and a second end 122 extending out of open end 108 of the syringe barrel 106. The second end 122 of the plunger rod 111 has a vial-receiving chamber 124 formed therein. A connection mechanism, such as a spike 126, is positioned within the vial-receiving chamber 124 for connecting the outlet 102 of the vial 100 thereto. In the prepackaged system described hereinabove, the vial 100 is provided in the vial-receiving chamber 124 during the manufacturing process and a flexible seal 128 is positioned over the second end 122 of the plunger rod 111 to maintain sterility of the contrast provided in the vial 100. In operation, a user engages the outlet 102 of the vial 100 with the spike 126 by applying pressure to the flexible seal 128. However, this is not to be construed as limiting the present invention as the vial 100 and the syringe/plunger rod combination may be provided as separate components with the second end 122 of the plunger rod 111 having an opening to allow the user to position a vial 100 within the vial-receiving chamber 124.

The plunger rod 111 further includes an intermediate sealing member 130 in sealing engagement with the inner wall 120 of the syringe barrel 106. The intermediate sealing member 130 is positioned between the first end 116 and the second end 122 of the plunger rod 111 such that the vacuum drive chamber 114 is provided between the intermediate sealing member 130 and the first end 116 of the plunger rod 111. In addition, if the vacuum drive chamber 114 and the delivery chamber 112 are provided with different diameters as discussed hereinabove and shown in FIGS. 2A-2C, then the first end 116 of the plunger rod 111 may be provided with a different diameter than the intermediate sealing member 130 and second end 122 of the plunger rod 111 as shown in FIGS. 2A-2C.

The plunger rod 111 also includes: a fluid channel 132 extending from the spike 126 to the first end 116 of the plunger rod 111; and a one-way check valve 134 positioned at the first end 116 of the plunger rod 111. While the plunger rod is disclosed herein as including a one-way check valve 134 positioned at the first end 116 of the plunger rod 111, this is not to be construed as limiting the present invention as the valve 134 may be positioned anywhere along the length of the channel 132. In addition, rather than utilizing a one-way check valve, a stopcock, a spring-loaded valve, or any other suitable valve may be utilized.

In addition, the fluid delivery device 10 includes an actuator 50, as discussed hereinabove, connected to the fluid dispensing end 110 of the syringe barrel 106. Desirably, the actuator 50 is a normally closed valve that may be manually operated or operated remotely via a controller 70 and remote controller 71.

In operation, fluid is dispensed from the vial 100 by connecting the outlet 102 thereof to the spike 126 by either applying force to the flexible seal 128 for the prepackaged system as discussed hereinabove or by positioning the vial 100 manually into the vial-receiving chamber 124 and engaging the outlet 102 thereof with the spike 126. This positions the outlet 102 of the vial 100 in fluid communication with fluid channel 132. Next, the second end 122 of the plunger rod 111 is pulled back in the direction of arrow $A_1$ to form a vacuum within the vacuum drive chamber 114. Due to the one-way check valve 134 at the first end 116 of the plunger rod 111 and the fluid channel 132 extending through the vacuum drive chamber 114 to the spike 126, the fluid from the vial 100 is drawn (by the vacuum) from the vial 100 into the delivery chamber 112 as shown by arrow $A_2$. Also, since the one-way check valve 134 is positioned at the first end 116 of the plunger rod 111 and the actuator 50 embodied as a normally closed valve positioned at the fluid dispensing end 110 of the syringe barrel 106, the device stays charged (due to the vacuum in the vacuum drive chamber 114) and does not deliver the fluid in the delivery chamber 112 until the actuator 50 is switched. At this point, the operator switches the actuator 50 (e.g., by opening the normally closed valve) from a first state in which fluid is prevented from flowing through the fluid dispensing end 110 of the syringe barrel 106 to a second state causing the plunger rod 111 to move in the direction of arrow $A_3$ to force the fluid within the delivery chamber 112 out of the fluid dispensing end 110.

Furthermore, two or more of injection device 10 described hereinabove can be "ganged together" with appropriate fluid path sets (not shown) to deliver multiple fluids to a patient (e.g., contrast followed by saline, stress agent followed by contrast followed by saline, etc.).

While the fluid-filled cartridge 40 has been described hereinabove as a contrast vial 100, this is not to be construed as limiting the present invention as any suitable fluid delivery device may be utilized. For instance, a syringe (not shown) may be utilized. In such an instance, the connection mechanism may be embodied as a female luer connector (not shown) instead of a spike 126.

Figure 3A:
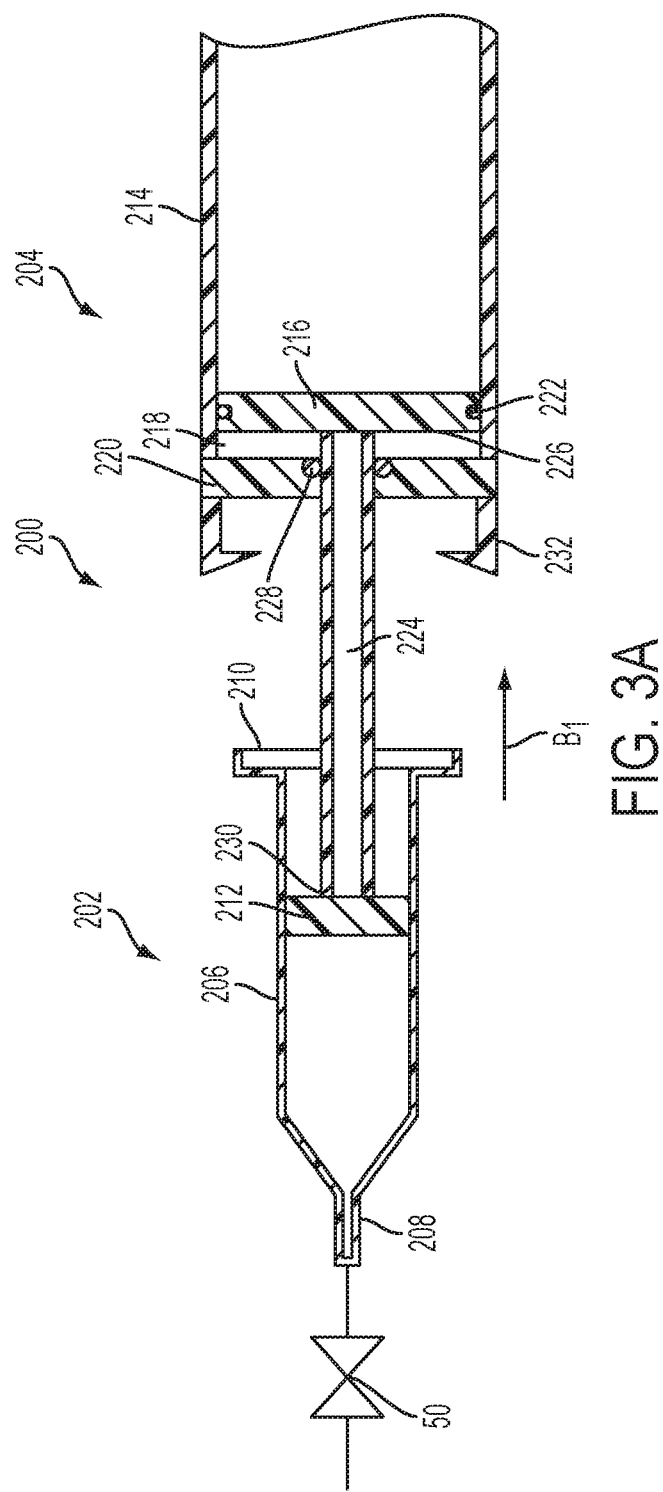
FIGS. 3A and 3B are a series of cross-sectional views of a second embodiment of the fluid delivery device of the present invention.
Figure 3B:
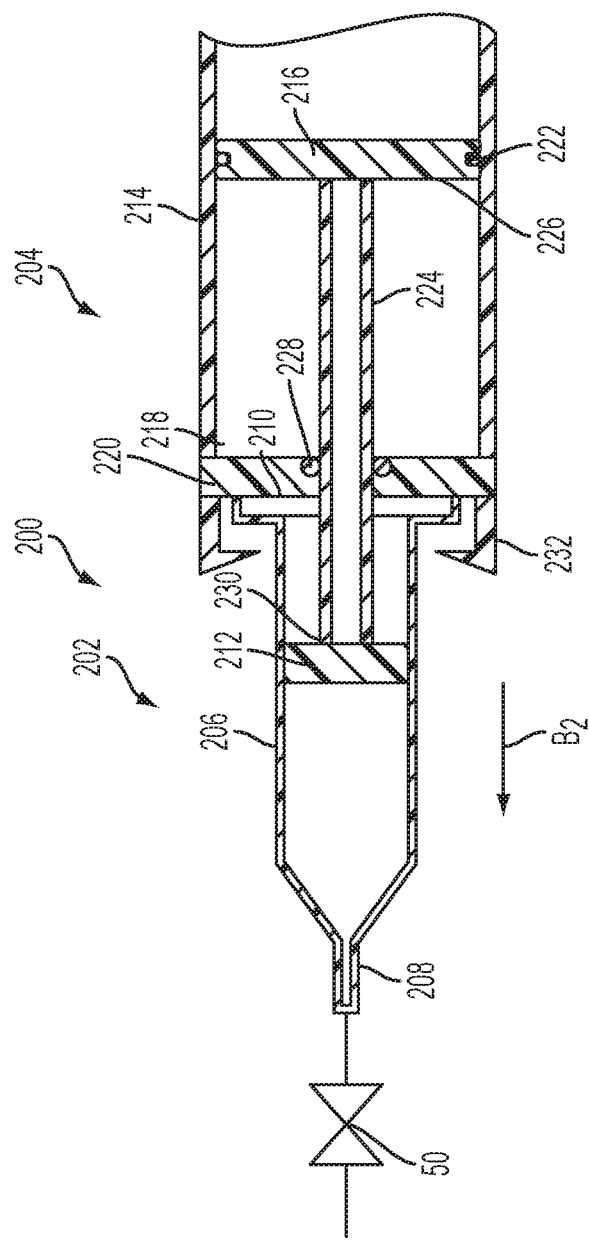

With reference to FIGS. 3A and 3B, an alternative embodiment of an injection device 200 includes: a syringe 202, a drive mechanism 204, and an actuator 50. The syringe 202 includes a substantially cylindrical syringe barrel 206 having a fluid dispensing end 208 and an open end 210 and a plunger 212 configured to be received within the open end 210 of the syringe barrel 206.

The drive mechanism 204 includes a substantially cylindrical body 214 having a movable member 216 positioned therein to form a chamber 218 between the movable member 216 and a substantially closed first end 220 of the cylindrical body 214. The movable member 216 includes a seal 222 which extends around a circumference thereof to fluidly isolate the chamber 218 from a second end of the cylindrical body 214.

The drive mechanism 204 also includes a plunger rod 224 connected to a first side 226 of the movable member 216 and extends through the first end 220 of the body 214. A seal 228 is provided between the first end 220 and the plunger rod 224 to prevent fluid from leaving the cylindrical body 214. The plunger rod 224 is configured to operatively engage a rear end 230 of the plunger 212 through a threaded or other type of connection. The drive mechanism 204 further includes a locking mechanism 232 configured to secure the open end 210 of the syringe 202 to the substantially closed first end 220 of the body 214. The drive mechanism 204 may be embodied as a disposable device where the locking mechanism 232 locks the syringe 202 onto the body 214 such that it cannot be removed.

In addition, the fluid delivery device 200 includes an actuator 50, as discussed hereinabove, connected to the fluid dispensing end 208 of the syringe barrel 206. Desirably, the actuator 50 is a normally closed valve that may be manually operated or operated remotely via a controller 70 and remote controller 71.

In operation, fluid is dispensed from the syringe 202 by connecting the syringe 202 to the plunger rod 224 by threadedly connecting a first end of the plunger rod 224 to the plunger 212. Thereafter, the open end 210 of the syringe 202 is forced into the locking mechanism 232 by moving the syringe 202 in the direction of arrow $B_1$, thereby moving the movable member 216 towards the second end of the cylindrical body 214 which forms a vacuum within the chamber 218. At this point, the operator switches the actuator 50 (e.g., by opening the normally closed valve) from a first state in which fluid is prevented from flowing through the fluid dispensing end 208 of the syringe barrel 206 to a second state causing the movable member 216, the plunger rod 224, and the plunger 212 to move in the direction of arrow $B_2$ to force the fluid within the syringe 202 out of the fluid dispensing end 208.

The syringe 202 for the injection fluid (generally an MR contrast fluid) can, for example, be a polymeric or glass MR syringe available, for example, from Bayer HealthCare LLC of Indianola, Pa. Such syringes can be purchased "prefilled" with injection fluid or can be purchased empty and filled at the MRI site. The fluid in such syringes is pressurized via the plunger 212, which is slidably disposed within the syringe barrel 206.

Figure 4A:
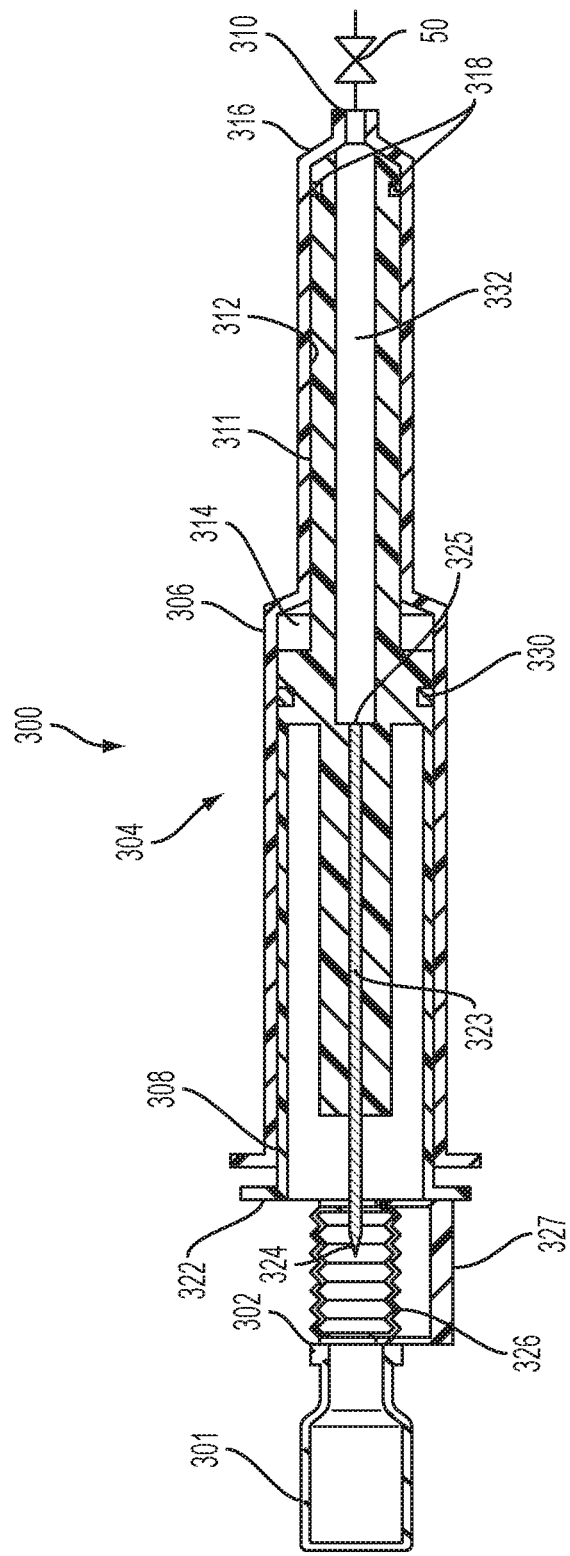
FIGS. 4A-4C are a series of cross-sectional views of a third embodiment of the fluid delivery device of the present invention.
Figure 4B:
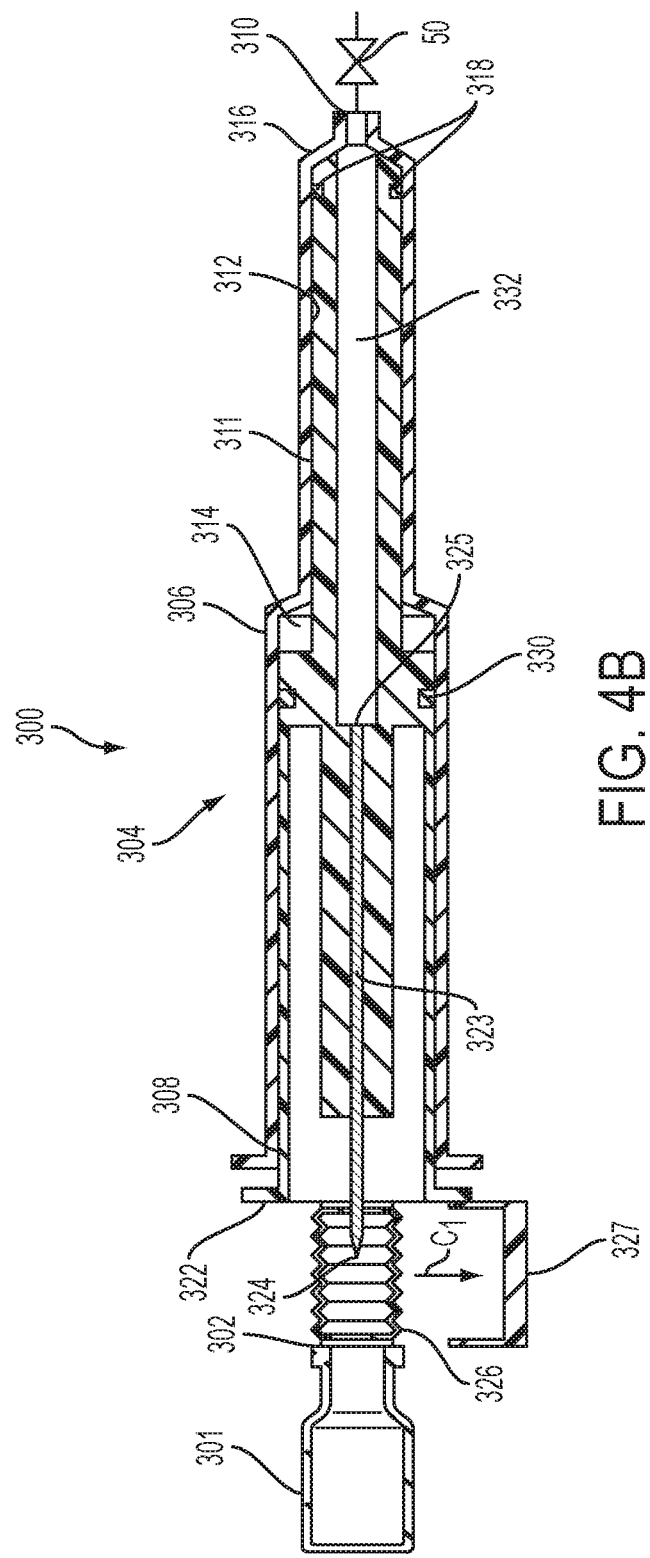
Figure 4C:
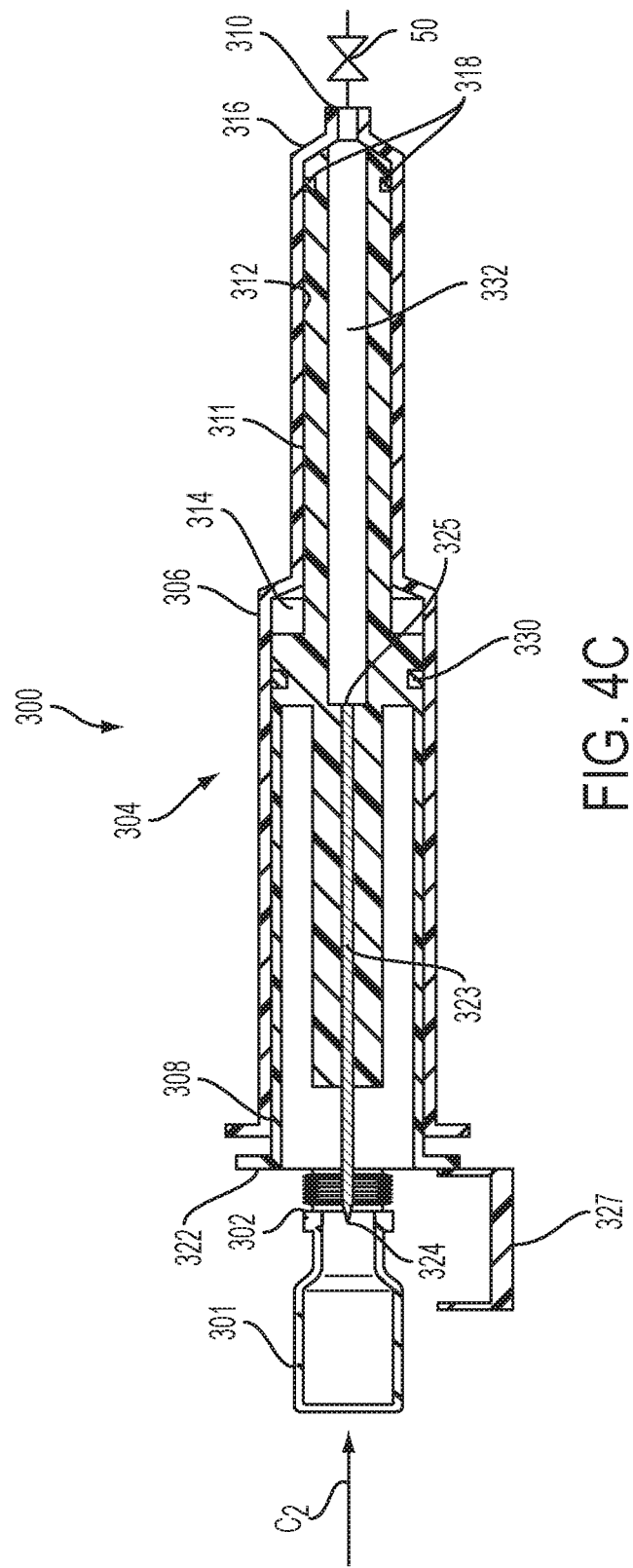

With reference to FIGS. 4A-4C, another alternative embodiment of the injection device 300 is illustrated. The injection device 300 is desirably provided as a prepackaged system that is sterilized. The injection device 300 includes an MR contrast vial 301 (as the fluid-filled cartridge) having a septum sealed outlet 302. The injection device 300 also includes a syringe 304 having a substantially cylindrical syringe barrel 306 that includes a fluid receiving end (i.e., open end 308) and a fluid dispensing end 310 and a plunger rod 311 configured to be received within the open end 308 of the syringe barrel 306. As discussed in greater detail hereinafter, the cylindrical syringe barrel 306 is divided into a delivery chamber 312 (in FIGS. 4A-4C the plunger rod is positioned within the deliver chamber) and a vacuum drive chamber 314. Desirably, the delivery chamber may have a first diameter and the vacuum drive chamber 314 may have a second diameter that is greater than the first diameter as shown in FIGS. 4A-4C; however, this is not to be construed as limiting the present invention as both chambers may have the same diameter. In addition, while the injection device 300 is described hereinabove, this is not to be construed as limiting the present invention as any suitable fluid container may be utilized.

The plunger rod 311 includes: a first end 316 having a sealing member, such as O-ring 318, provided in sealing engagement with an inner wall of the syringe barrel 306 to form the delivery chamber 312 between the first end 316 of the plunger rod 311 and the fluid dispensing end 310 of the syringe barrel 306; and a second end 322 extending out of open end 308 of the syringe barrel 306. The second end 322 of the plunger rod 311 has a connection mechanism, such as a spike 323, extending therefrom and comprising a fluid path extending from a first end 324 of the spike 323 to a second end 325 of the spike 323 in fluid communication with the delivery chamber 312 of the syringe 304. A compressible member 326 extends from the outlet 302 of the vial 301 to the open end 308 of the syringe barrel 306 and surrounds at least the first end 324 of the spike 323. A removable retention mechanism 327 is positioned between the outlet 302 of the vial 301 and the open end 308 of the syringe barrel 306 over the compressible member to prevent the outlet 302 of the vial 301 from contacting the spike 323.

In operation, a user removes the retention mechanism in the direction of arrow $C_1$ as shown in FIG. 4B. A user then engages the outlet 302 of the vial 301 with the spike 323 by applying pressure to the vial 301 in the direction of arrow $C_2$ as shown in FIG. 4C, thereby compressing the compressible member 326.

The plunger rod 311 further includes an intermediate sealing member 330 in sealing engagement with the inner wall of the syringe barrel 306. The intermediate sealing member 330 is positioned between the first end 316 and the second end 322 of the plunger rod 311 such that the vacuum drive chamber 314 is provided between the intermediate sealing member 330 and the first end 316 of the plunger rod 311. In addition, if the vacuum drive chamber 314 and the delivery chamber 312 are provided with different diameters as discussed hereinabove and shown in FIGS. 4A-4C, then the first end 316 of the plunger rod 311 may be provided with a different diameter than the intermediate sealing member 330 and second end 322 of the plunger rod 311 as shown in FIGS. 4A-4C.

The plunger rod 311 also includes: a fluid channel 332 extending from the second end 325 of the spike 323 to the first end 316 of the plunger rod 311; and a one-way check valve positioned at the first end 316 of the plunger rod 311.

In addition, the injection device 300 includes an actuator 50, as discussed hereinabove, connected to the fluid dispensing end 310 of the syringe barrel 306. Desirably, the actuator 50 is a normally closed valve that may be manually operated or operated remotely via a controller 70 and remote controller 71.

In operation, fluid is dispensed from the vial 301 by connecting the outlet 302 thereof to the spike 323 as discussed hereinabove. This positions the outlet 302 of the vial 301 in fluid communication with fluid channel 332. Next, the injection device 300 is operated in the same manner as the injection device 10 as discussed in detail hereinabove.

Desirably, the injection devices discussed hereinabove are suitable to be placed within one foot of the MRI bore. More desirably, the injection devices of the present disclosure are suitable to be placed within the bore, thereby providing close access to the injection site on the patient and eliminating lengthy connective tubing used with many currently available injection devices. In general, to be "MR compatible" as that phrase is used herein, the materials of injection device 10, injection device 200, and injection device 300 should not interfere with the operation of an MR scanner in a substantial manner (for example, to cause image artifacts). Additionally, the MR environment (for example, the powerful magnetic field) should not substantially interfere with the operation of the injection device 10, injection device 200, and injection device 300. Examples of suitable MRI compatible materials for injection device 10, injection device 200, and injection device 300 include, but are not limited to, polymeric materials, glass materials, and aluminum.

While specific embodiments of the device of the present disclosure have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the device of the present disclosure which is to be given the full breadth of the claims appended and any and all equivalents thereof.

The invention claimed is:

1. A fluid delivery device comprising:
a fluid-filled cartridge comprising an outlet;
a syringe comprising a substantially cylindrical syringe barrel having an open end and a fluid dispensing end;
a plunger rod configured to be received within the open end of the syringe barrel, the plunger rod comprising: a first end having a sealing member provided in sealing engagement with an inner wall of the syringe barrel such that a first syringe chamber is provided between the first end of the plunger rod and the fluid dispensing end of the syringe barrel; a second end extending out of the open end of the syringe barrel and having a cartridge-receiving chamber having a connection mechanism positioned therein for connecting the outlet of the cartridge thereto; an intermediate sealing member in sealing engagement with the inner wall of the syringe barrel, the intermediate sealing member positioned between the first end and the second end of the plunger rod such that a second syringe chamber is provided between the intermediate sealing member and the first end of the plunger rod; and a fluid channel extending from the connection mechanism to the first end of the plunger rod; and
an actuator connected to the fluid dispensing end of the syringe barrel,
wherein fluid is dispensed from the cartridge by connecting the outlet of the cartridge to the connection mechanism, thereby providing the cartridge in fluid communication with the fluid channel, forming a vacuum within the second syringe chamber by enlarging a volume of the second syringe chamber by pulling the second end of the plunger rod away from the open end of the syringe barrel which moves the intermediate sealing member closer to the open end of the cylindrical barrel, thereby drawing fluid from the cartridge through the fluid channel and into the first syringe chamber, and switching the actuator from a first state in which fluid is prevented from flowing through the fluid dispensing end of the syringe to a second state to allow the fluid to flow through the fluid dispensing end.

2. The fluid delivery device of claim 1, wherein the fluid-filled cartridge is a vial and the connection mechanism is a spike.

3. The fluid delivery device of claim 2, wherein the vial is positioned within the cartridge receiving chamber, a flexible seal is positioned over the second end, and the vial is engaged with the spike by pressing the flexible seal.

4. The fluid delivery device of claim 1, wherein the fluid-filled cartridge is a syringe and the connection mechanism is a female luer connector.

5. The fluid delivery device of claim 1, wherein the first syringe chamber has a first diameter and the second syringe chamber has a second diameter that is greater than the first diameter.

6. The fluid delivery device of claim 1, wherein a mechanism of the actuator comprises a rotary valve, a pinch valve with tubing, a ratchet valve, a fusible link, a trumpet valve, a port closing valve, a pump system, or a drive system.

7. The fluid delivery device of claim 1, further comprising a controller configured to remotely control the state of the actuator.

8. The fluid delivery device of claim 7, wherein the controller controls the state of the actuator via ultrasound, via a protocol of an imaging scanner, via microwave energy, via a mechanical link, via infrared light, via fiber optic cable, via pneumatic power, via hydraulic power, via voice activation, via movement of a scanner table, via time delay, via an RF gradient trigger from a scanner, via a photo cell, via optical light, via an RF signal, or via line power.

9. The fluid delivery device of claim 1, wherein the fluid-filled cartridge, the syringe, the plunger rod, and the actuator are MR compatible, thereby making the device suitable for use in or near a bore of an MR scanner.

10. The fluid delivery device of claim 1, wherein the plunger rod further comprises a valve positioned along the fluid channel of thereof.

11. The fluid delivery device of claim 10, where the valve is one of a one-way check valve, a stopcock, and a spring-loaded valve.

* * * * *

UNITED STATES PATENT AND TRADEMARK OFFICE
CERTIFICATE OF CORRECTION

| | |
|---|---|
| PATENT NO. | : 11,602,591 B2 |
| APPLICATION NO. | : 16/746377 |
| DATED | : March 14, 2023 |
| INVENTOR(S) | : Kevin P. Cowan |

It is certified that error appears in the above-identified patent and that said Letters Patent is hereby corrected as shown below:

In the Claims

In Column 12, Line 14, in Claim 10, delete "channel of" and insert -- channel --, therefor.

Signed and Sealed this
Eleventh Day of July, 2023

Katherine Kelly Vidal
*Director of the United States Patent and Trademark Office*